United States Patent
Pearson

(10) Patent No.: US 7,375,142 B2
(45) Date of Patent: May 20, 2008

(54) PROCESS AND APPARATUS FOR THE PRODUCTION OF USEFUL PRODUCTS FROM CARBONACEOUS FEEDSTOCK

(75) Inventor: Stanley R. Pearson, Baton Rouge, LA (US)

(73) Assignee: Pearson Technologies, Inc., Aberdeen, MS (US)

( * ) Notice: Subject to any disclaimer, the term of this patent is extended or adjusted under 35 U.S.C. 154(b) by 160 days.

(21) Appl. No.: 10/568,402

(22) PCT Filed: Aug. 20, 2004

(86) PCT No.: PCT/US2004/027172

§ 371 (c)(1),
(2), (4) Date: Feb. 13, 2006

(87) PCT Pub. No.: WO2005/021474

PCT Pub. Date: Mar. 10, 2005

(65) Prior Publication Data

US 2007/0010588 A1    Jan. 11, 2007

(51) Int. Cl.
C07C 27/00    (2006.01)
(52) U.S. Cl. .................. 518/706; 518/702; 518/704; 518/713; 518/715
(58) Field of Classification Search ............... 518/702, 518/704, 706, 713, 715
See application file for complete search history.

(56) References Cited

U.S. PATENT DOCUMENTS

| | | | |
|---|---|---|---|
| 2,460,508 A | 2/1949 | Johnson et al. |
| 2,649,468 A | 8/1953 | Benedict et al. |
| 4,348,487 A | 9/1982 | Goldstein et al. |
| 4,409,405 A | 10/1983 | Lin et al. |
| 4,913,842 A | 4/1990 | Yoneoka et al. |
| 5,073,356 A | 12/1991 | Guro et al. |
| 5,763,716 A | 6/1998 | Benham et al. |
| 5,767,165 A | 6/1998 | Steinberg et al. |
| 6,028,119 A | 2/2000 | Kokubu et al. |
| 6,191,174 B1 | 2/2001 | Early et al. |
| 6,218,439 B1 | 4/2001 | Kobayashi et al. |
| 6,232,352 B1 | 5/2001 | Vidalin |
| 6,274,096 B1 | 8/2001 | Thiebaut et al. |
| 6,300,380 B1 | 10/2001 | Kobayashi et al. |
| 6,444,712 B1 | 9/2002 | Janda |
| 6,486,219 B1 | 11/2002 | Janda et al. |
| 6,495,610 B1 | 12/2002 | Brown |
| 6,512,018 B2 | 1/2003 | Kennedy |
| 6,531,630 B2 | 3/2003 | Vidalin |
| 6,534,551 B2 | 3/2003 | Allam et al. |
| 6,599,491 B2 | 7/2003 | Vidalin |
| 6,632,846 B2 | 10/2003 | Sheppard et al. |
| 6,673,845 B2 | 1/2004 | Price |
| 6,696,501 B2 | 2/2004 | Schanke et al. |
| 6,706,770 B2 | 3/2004 | Patel et al. |
| 6,747,067 B2 | 6/2004 | Melnichuk et al. |
| 6,946,493 B2 | 9/2005 | Mohedas et al. |
| 6,958,363 B2 | 10/2005 | Espinoza et al. |
| 2003/0083390 A1 | 5/2003 | Shah et al. |
| 2004/0180971 A1 | 9/2004 | Inoue et al. |
| 2005/0113463 A1 | 5/2005 | O'Rear et al. |
| 2005/0113465 A1 | 5/2005 | O'Rear et al. |
| 2005/0113466 A1 | 5/2005 | Guillard et al. |
| 2005/0137269 A1 | 6/2005 | Hershkowitz et al. |

FOREIGN PATENT DOCUMENTS

| | | |
|---|---|---|
| GB | 2025418 A | 1/1980 |
| GB | 2110558 A | 6/1983 |
| GB | 2134601 A | 8/1984 |
| GB | 2139224 A | 11/1984 |
| GB | 2162172 A | 1/1986 |

OTHER PUBLICATIONS

Database CAPLUS on STN, Chemical Abstract (Columbus OH,US) CA: 107:136324, Alberta Gas Chemincal Ltd "Manufacture of Alcohol and Catalysts for use" NL 8502813, 1987.

Primary Examiner—J. Parsa
(74) Attorney, Agent, or Firm—Orrick, Herrington & Sutcliffe LLP

(57) ABSTRACT

A carbonaceous feedstock to alcohol conversion process in which carbon dioxide and a portion of the hydrogen produced are removed from the syngas stream issuing from a feedstock reformer, to yield a reduced hydrogen, carbon monoxide and methane syngas stream. The hydrogen and the carbon dioxide are passed through a Fischer Tropsch reactor which is catalyzed to favor the production of methanol. The methanol produced in the Fischer-Tropsch reactor is passed with the reduced hydrogen syngas through a second Fischer-Tropsch reactor which is catalyzed to favor the production of ethanol. Also disclosed, without limitation, are a unique catalyst, a method for controlling the content of the syngas formed in the feedstock reformer, and a feedstock handling system.

56 Claims, 4 Drawing Sheets

PROCESS AND APPARATUS FOR THE PRODUCTION OF USEFUL PRODUCTS FROM CARBONACEOUS FEEDSTOCK

BACKGROUND OF THE INVENTION

The present invention relates to the conversion of carbonaceous feedstock into useful products. The term "carbonaceous feedstock" as used herein includes not only organic matter that is part of the stable carbon cycle, but also fossilized organic matter such as coal, petroleum, and natural gas, and products, derivatives and byproducts thereof such as plastics, petroleum coke and the like. The first step in such processes is the gasification of the feedstock in a so-called "reformer" to a stream of hydrogen, carbon monoxide, carbon dioxide and methane. This stream is referred to as syngas, and its generation is disclosed in U.S. Pat. No. 4,872,886, and others. The '886 patent includes an oxidation first step, in which air is used to fire a portion of the feedstock. The resulting stream is then combined with a "coal slurry" stream in a second stage of the conversion reaction. U.S. Reissue 35,377 discloses the anaerobic reaction of the feedstock with steam.

The various ingredients in a stream of syngas can then be converted into other compounds in a so-called Fischer-Tropsch reactor. The catalyst used in the reactor, and to some extent the temperatures and pressures used, will determine what products can be obtained.

The Fischer-Tropsch reaction disclosed at the bottom of page 106 in *Organic Chemistry*, Third Edition, by Brewster and McEwen, ©1961 shows the conversion of carbon monoxide and hydrogen to alkanes over a cobalt-thoria catalyst. U.S. Pat. No. 4,752,622 discloses and claims the use of a three component catalyst comprising molybdenum or tungsten, cobalt or nickel, and an alkali or alkaline earth promoter, to produce methanol from carbon monoxide and hydrogen. U.S. Pat. No. 4,609,679 selectively catalyzes for the production of methane, by using ruthenium combined with tantalum, niobium, vanadium or mixtures thereof. U.S. Pat. No. 4,675,344 (Canadian CA 1,267,160) controls the ratio of methanol to higher alcohols produced by using molybdenum or tungsten sulfide catalysts, and adjusting the concentration of a sulfur releasing substance in the feed.

The conversion of methanol to ethanol and higher alcohols in the presence of carbon monoxide and hydrogen is disclosed in U.S. Pat. No. 4,825,013 and its Canadian counterpart CA 1,268,189. The patent claims achieving this conversion through the use of a heterogeneous catalyst comprised of molybdenum or tungsten and an alkali or alkaline earth element.

German Patent Application 32 42 697 A1 is directed towards a process for the concurrent production of methanol and ethanol by catalytically converting synthesis gas into methanol and separating the methanol from the reaction mixture. The separated methanol, along with excess gas remaining, is converted to ethanol at an increased pressure and an increased temperature, using a cobalt catalyst. In this process methanol, as well as ethanol, is produced from a single raw substance in a two-step process, using a heterogeneously catalyzed system with a homogeneously catalyzed system. Fresh synthesis gas is added if the excess gas does not contain enough carbon monoxide prior to homologization.

In European patent application 849,245, natural gas is converted in a reformer to a syngas stream of carbon monoxide, carbon dioxide, hydrogen and unconverted methane. This entire syngas stream is passed through a Fischer-Tropsch reactor to produce methanol. The unreacted syngas is divided into a CO, $CO_2$ and $CH_4$ stream, which is recycled back through the reformer; and a hydrogen rich stream, which is combined with oxygen and combusted to provide heat for the reformer.

PCT patent application WO 82/02547 removes $CO_2$ from a syngas stream and recycles it through a reformer along with steam and an incoming stream of methane. The reactants produce a syngas stream from which the $CO_2$ is thus continuously removed and recycled.

European patent application 253,540 is exemplary of art in which higher alcohols are produced in a Fischer-Tropsch reactor from feedstock (coal slurry) syngas, and any methanol produced is recycled through the Fischer-Tropsch reactor.

SUMMARY OF THE INVENTION

One aspect of the present invention comprises a carbonaceous feedstock to alcohol conversion process in which carbon dioxide and a portion of the hydrogen produced are removed from the syngas stream issuing from a feedstock reformer, to yield a second syngas stream comprising carbon monoxide and a reduced amount of hydrogen. The hydrogen and the carbon dioxide are passed through a Fischer-Tropsch reactor which is catalyzed to favor the production of methanol. The methanol produced in the Fischer-Tropsch reactor is passed with the reduced hydrogen syngas through a second Fischer-Tropsch reactor which; is catalyzed to favor the production of ethanol.

In a preferred aspect of the invention, methane is at least from time to time removed from the ethanol product stream and recycled with steam through a methane reformer to form carbon monoxide and hydrogen. These are then recycled into the syngas stream from the feedstock reformer.

Other aspects of the invention include, without limitation, a unique catalyst, a method for controlling the content of the syngas formed in the feedstock reformer, and a feedstock handling system. These and other features, advantages and aspects of the invention will be more fully understood and appreciated by reference to the written specification and appended drawings.

DETAILED DESCRIPTION OF THE PREFERRED EMBODIMENT

Introduction

Figure 1:
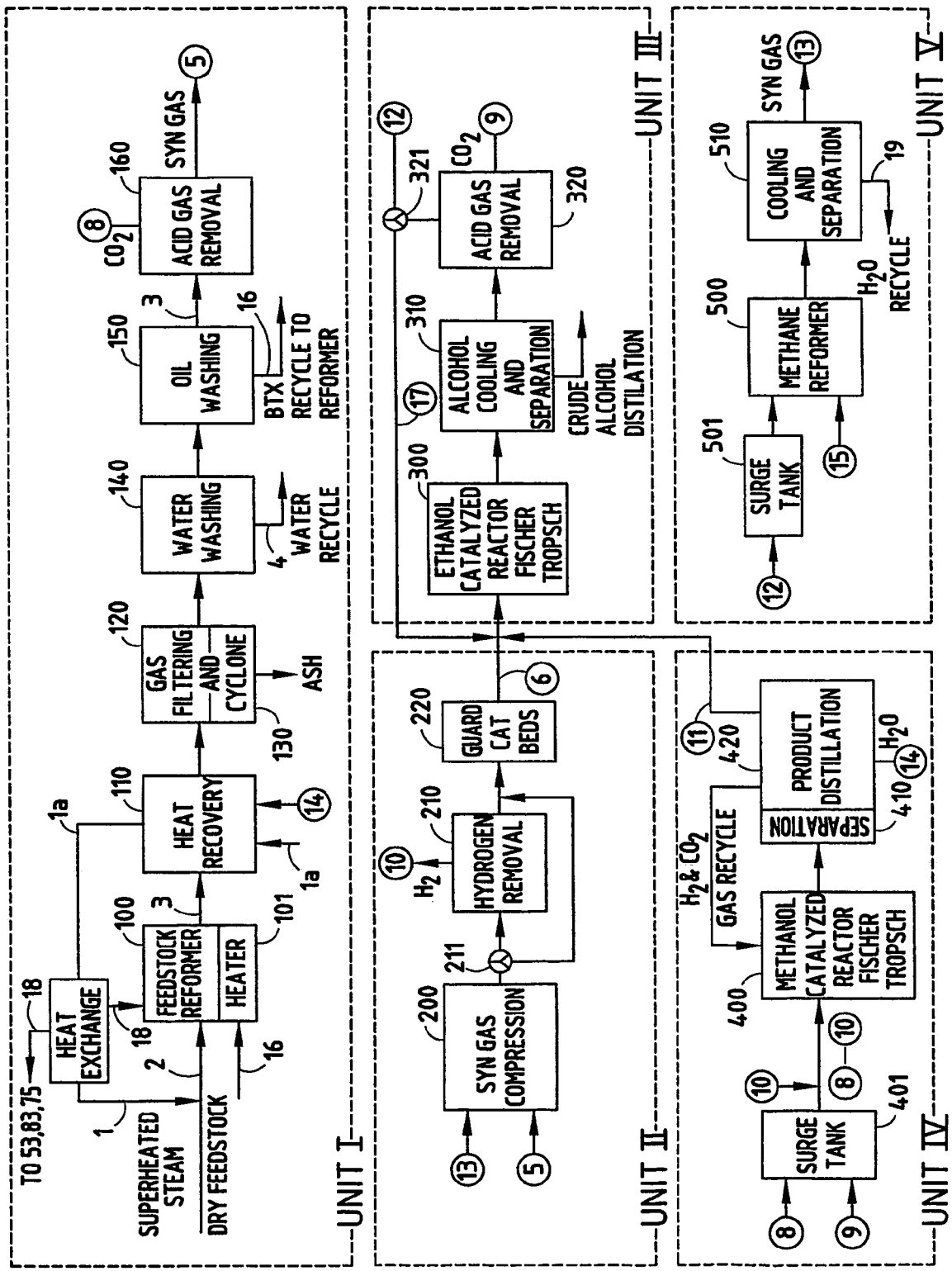
FIG. 1 is a process flow sheet identifying the basic operations conducted in a preferred embodiment of the invention.

The preferred embodiment apparatus employed is conveniently divided into five "Units" in FIG. 1. In Unit I, feedstock is converted to syngas (stream 3), and carbon dioxide (stream 8) is removed from syngas stream 3 In Unit II, hydrogen (stream 10) is partially removed from the syngas stream. In Unit III, syngas and methanol are converted to ethanol. In Unit IV, removed hydrogen and carbon dioxide are converted to methanol, which is used to feed the ethanol Fischer-Tropsch reactor 300 in Unit III. In Unit V, methane in stream 12 is reacted with steam (stream 15) to convert it to carbon monoxide and hydrogen (stream 13), which are fed into the syngas stream 5 in Unit II.

In the preferred embodiment, the alcohol production process generally involves the following steps (see FIG. 1).

1. Anaerobically reacting feedstock 2 with superheated steam 1 in feedstock reformer 100 (Unit I) to generate a syngas stream 3 of hydrogen, carbon monoxide, carbon dioxide and methane;
2. Removing the $CO_2$ (stream 8 from Unit I) to yield syngas stream 5, and removing a portion of the hydrogen (stream 10 from Unit II) from syngas stream 5 (and from syngas stream 13, which has been combined with syngas stream 5) to yield syngas stream 6, which comprises hydrogen, carbon monoxide and methane;
3. Passing the $CO_2$ (stream 8) and removed hydrogen (stream 10) through Fischer-Tropsch reactor 400 in Unit IV, catalyzed to favor the production of methanol (stream 11);
4. Passing the hydrogen, carbon monoxide and methane syngas stream 6, and methanol stream 11, through a Fischer-Tropsch reactor 300 in Unit III, catalyzed to favor ethanol production;
5. Diverting from time to time at least a portion (stream 12) of the unreacted syngas stream 17, which is recycling through the ethanol reactor 300, and reforming the methane it contains with steam in methane reformer 500 (Unit V), into carbon monoxide and hydrogen (stream 13); and
6. Recycling the resulting hydrogen and carbon monoxide stream 13 into Unit II along with the syngas stream 5 from the feedstock reformer 100, where they join and are compressed, and stripped of some hydrogen as discussed above, to form syngas stream 6, which is fed to ethanol reactor 300.

Whereas prior art carbonaceous feedstock conversion processes yield about 424 liters (112 gallons) of ethanol per ton of feedstock, and prior art fermentation processes yield about 379 liters (100 gallons) of ethanol per ton of feedstock, the present alcohol production process yields 757 liters (200 gallons) or more of ethanol per ton of feedstock.

Unit I: The Feedstock Reformer (FR)

In Unit I, feedstock 2 is anaerobically reformed in feedstock reformer 100 with superheated steam 1 into a syngas stream 3 comprising as its primary components hydrogen, carbon dioxide, carbon monoxide and methane. Minor amounts of other ingredients may be formed. Preparation of the feedstock prior to introduction into feedstock reformer 100 is illustrated in FIG. 3.

Figure 3:
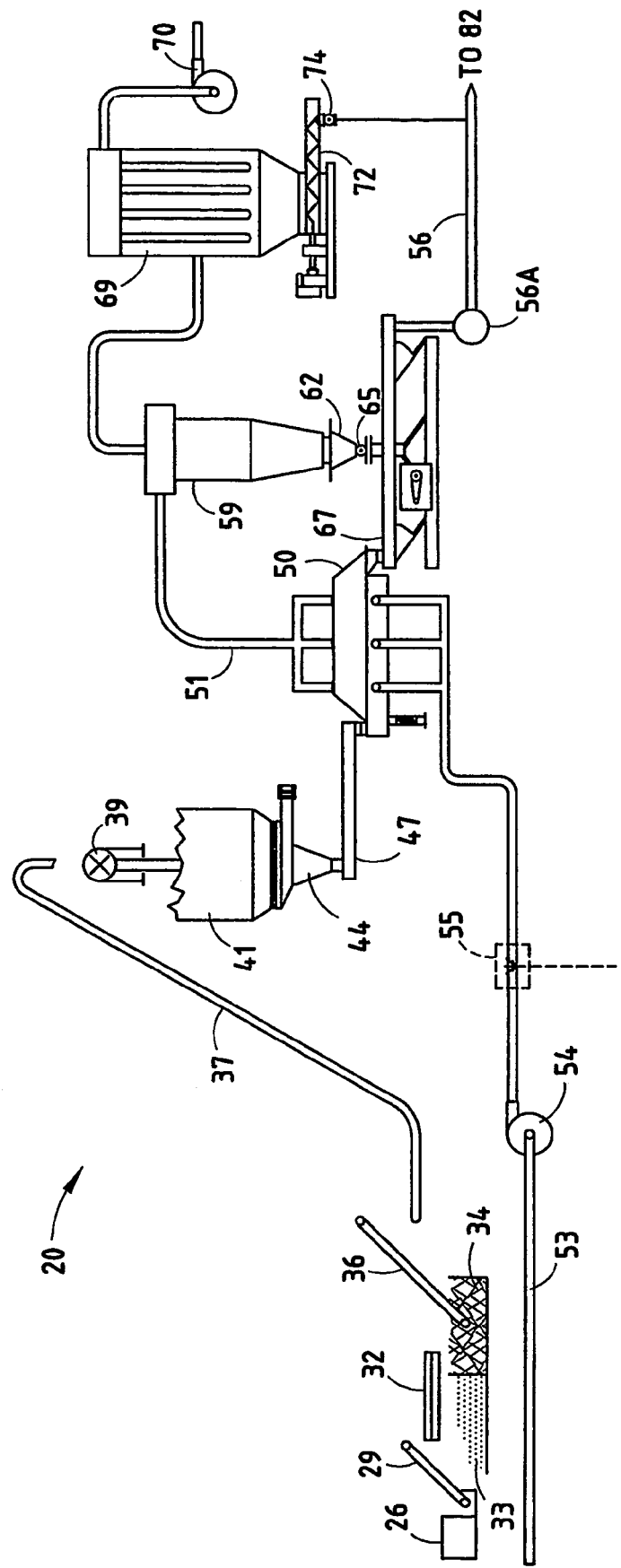
FIG. 3 is an illustration of the feedstock preparation apparatus.

Referring to FIG. 3, feedstock preparation apparatus 20 includes a rough grinder 26 which may be used depending on the consistency of feedstock. The feedstock is primarily wood and/or other organic material. Rough grinder 26 may be used if the feedstock is clumped together, in unusually large conglomerates, or if the feedstock needs to be further ground before being subjected to screen 32. After the feedstock is optionally subjected to rough grinder 26, feedstock is conveyed by first conveyor 29 to a position above screen 32. Feedstock falls off the first conveyor 29 to screen 32 where dirt 33 and iron are separated from feedstock. Iron removal is accomplished by appropriate placement of magnets. Feedstock is separated to a location 34 at the beginning of the second conveyor 36. Second conveyor 36 carries the feedstock to conveyor 37. Conveyor 37 carries feedstock to feed mill 39. Feed mill 39 comprises a grinder which grinds the feedstock to a size allowing it to pass through a 4.8 millimeter (3/16-inch) screen. After passing through the 4.8 millimeter (3/16-inch) screen, the feedstock falls into feed storage bin 41. For a plant having a feedstock feed rate of about 181 kilograms (400 lbs.) per hour, feed storage bin 41 is about 3 meters (10 feet) in diameter and about 3 meters (10 feet) tall. From feed storage bin 41, feedstock is placed in vibrating bin discharger 44. A vibrating dryer feed conveyor 47 then moves feedstock from vibrating bin discharger 44 to dryer 50, where the feedstock is dried to a moisture content of from about 5% to about 20%, more preferably from about 9% to about 15%.

Flue gas inlet 53 feeds flue gas (stream 18 from the heat source of feedstock reformer 100) into wood dryer system 50. Flue gas inlet 53 may contain compressor 54 and/or fuel gas start-up combuster 55. Fuel gas up-start combuster 55 is usually not necessary. However, if the drier has been shut down, combuster 55 ignites a stream of fuel gas which is fed into the flue gas stream at combuster 55. Any fuel may be employed.

The flue gas is fed into dryer 50 and mixes with communited feedstock to dry it, purge it and heat it for further processing. The flue gas comprises about 80% nitrogen and 20% $CO_2$. From dryer 50 fines and smaller feedstock particles are carried by flue gas out through drier stack 51 to a cyclone separator 59, while larger feedstock particles pass along a vibrating screen at the bottom of dryer 50, out through one end thereof, where they are deposited on enclosed vibrating screen conveyor 67. Cyclone separator 59 separates the fines from the remaining smaller feedstock particles. The smaller feedstock particles flow down to dryer cyclone dust collector 62, and then pass from dryer cyclone dust collector 62 through solids outlet airlock 65, wherein the smaller particles of feedstock are then reunited with the larger particles of feedstock on vibrating screen feed conveyor 67.

Figure 4:
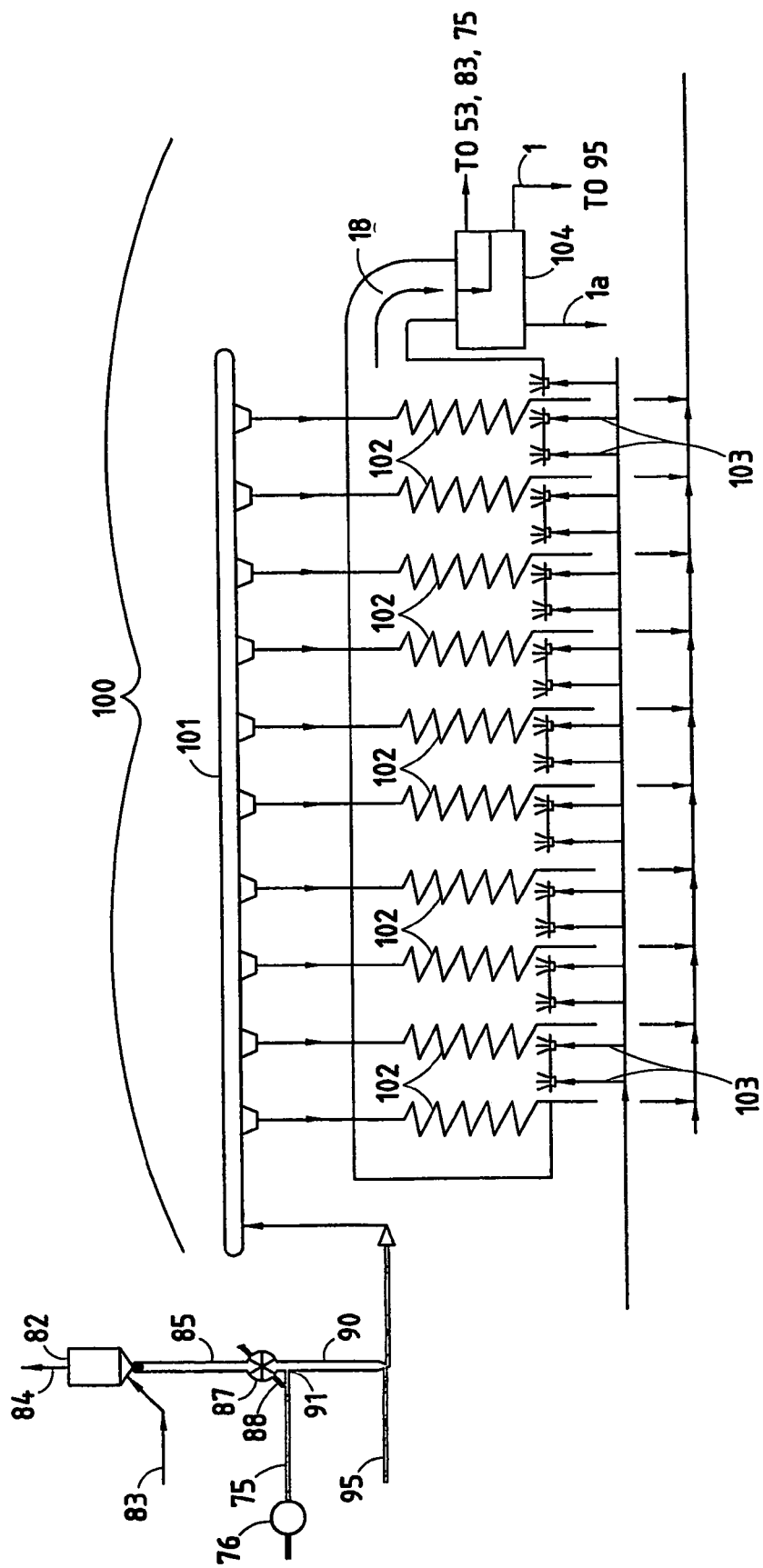
FIG. 4 is an illustration of the feedstock reformer.

The vibrating screen feed conveyor 67 conveys the dried feedstock to blower 56A, which blows the dried comminuted feedstock, along with the inert flue gas, through pipe 56. The use of flue gas as a "carrier" minimizes the introduction of air into the system. The dried feedstock particles are fed by blower 56A through feed pipe 56 to bunker 82 (FIG. 4). The fines of feedstock are then vented from separator 59 and carried to bag house dust collector 69. The fines are carried by the flue gas flow, induced in part by blower 70. The fines of feedstock which fall to the bottom of bag house dust collector 69 are fed via screw conveyor 72 through rotary airlock 74. They are fed into the flow of large and small particles of feedstock being carried via a flue gas in feed pipe 56.

Blower 70 and blower 54 are balanced so as to maintain a relatively neutral pressure in vibrating screen drier 50. There is just enough of a pressure difference to keep the flue gas flowing through drier 50.

Feedstock is fed via flue gas feed pipe 56, to feed hopper or bunker 82 (FIG. 4). A purge gas inlet 83 feeds flue gas into hopper 82. Being about 80% nitrogen and about 20% carbon dioxide, flue gas helps insure that the reformation process in reformer 100 will be carried out anaerobically. Hopper 82 also includes a vent 84 for venting flue gas.

Figure 5:
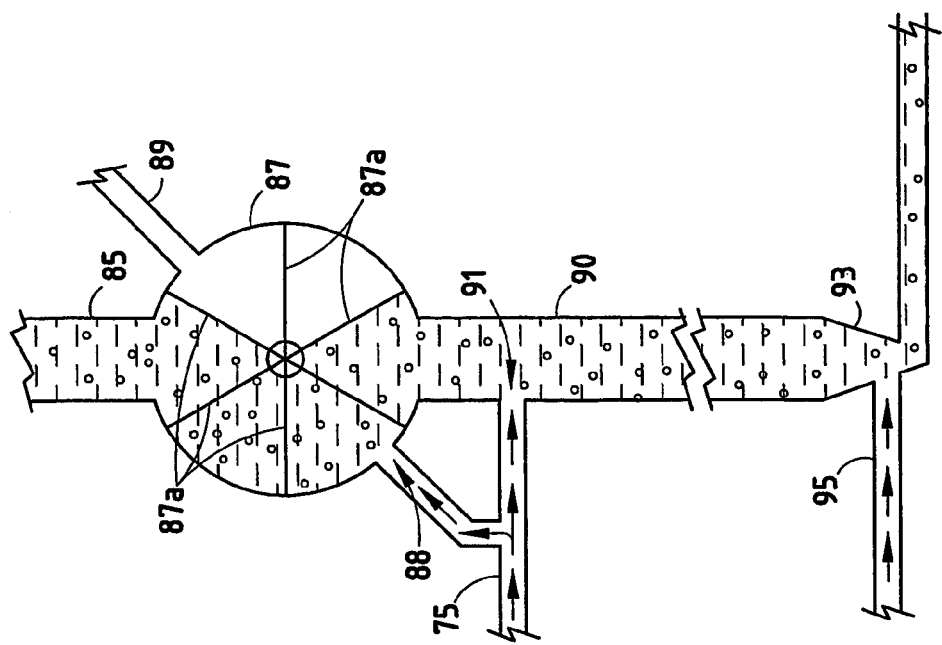
FIG. 5 is a cross-sectional view of the feedstock metering and steam mixing apparatus.

From hopper 82, feedstock settles into tube 85, which extends from the bottom of hopper 82. The feedstock is metered by rotary valve 87 into feed tube 90, at the bottom of which it is entrained with steam under pressure entering from steam line 95. To keep feedstock flowing into the stream of steam, and in order to counter steam back pressure in pipe 90, a supply of flue gas 18 is moved through line 75 via compressor 76 to inlet 91 near the top of feed tube 90 (FIGS. 4 and 5). To prevent the pressure in tube 90 from blowing feedstock back into rotary valve 87, some of the flue gas is also split off from line 75 and fed to inlet 88 of rotary valve 87. Rotary valve 87 includes a central rotor having a plurality of vanes 87a which divide the interior of valve 87 into separate compartments. Opposite inlet 88 on rotary valve 87, is outlet pressure vent 89. As the rotor of valve 87 rotates counterclockwise, the compartment formed by vanes 87a at the top fill with feedstock. That filled compartment is then rotated counterclockwise until it opens to inlet 88, where it is pressurized with incoming flue gas. As the rotor rotates further, the feedstock filled and pressurized chamber opens into feed tube 90. Since the pressure in the rotor chamber is equalized with the pressure in tube 90, the feedstock falls down into tube 90. As the valve rotor continues on its counterclockwise journey, it is eventually vented through vent 89, such that when the chamber reaches feed tube 85 again, it is depressurized and will not vent back up into feed tube 85. After feedstock has moved through rotary valve 87 and into feed tube 90, it feeds by gravity into mixing chamber 93 at the bottom of tube 90, where superheated steam (510° C. (950° F.) steam) from steam line 95 is mixed with feedstock.

Superheated steam carries the feedstock to feedstock reformer 100 (FIG. 4). In the process of heating up the feedstock, the steam cools to approximately 204° C. (400° F.) as the superheated steam and feedstock approach wood reformer 100. Within feedstock reformer 100 a flow divider 101 distributes the cooled steam and feedstock into about 76 millimeter (3-inch) diameter tubing coils 102 through which steam and feedstock pass. Feedstock reformation carried out in feedstock reformer 100 is endothermic. Heat for the feedstock reformation process is provided by burners 103 at the bottom of feedstock reformer 100. Excess syngas or any other fuel can be burned in burners 103 at the bottom of reformer 100. The flue gas 18 from burners 103 passes through a heat exchanger 104, used to help superheat the incoming stream of water 1a to superheated steam 1, and then into flue gas lines 53, 83 and 75 (FIG. 4). For greater energy independence of the overall process, even more excess syngas can be made and used to run a turbine and generate electricity to power the compressors and other electrically driven devices.

The inlet temperature of the feedstock and superheated steam 1 entering feedstock reformer 100 is about 204° C. (400° F.) The exit temperature of the syngas leaving feedstock reformer 100 is between 871° C. (1600° F.) and 1204° C. (2200° F.), preferably about 898° C. (1650° F.) to about 926° C. (1700° F.) At 1093° C. (2000° F.) and above, with a contact time of 5.0 seconds, one obtains less than one mole percent of methane and a great deal of $CO_2$, which is an undesirable result. Pressure in feedstock reformer 100 does not appear to be critical. The reformer is preferably run at a pressure of about 241 kilopascals (KPa) (35 psig) to about 276 KPa (40 psig).

Figure 2:
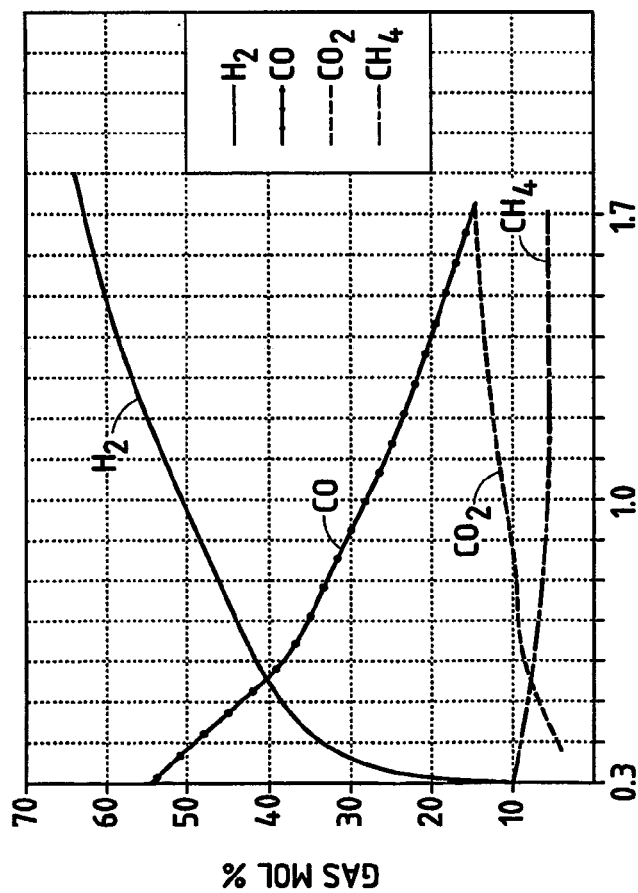
FIG. 2 is a graph illustrative of the variation in syngas products which one achieves as a function of the temperature, contact time of the gas in the feedstock reformer, the ratio of hydrogen, carbon and oxygen in the feedstock used and the ratio of steam to feedstock fed to the reformer.

For any given feedstock, one can vary the proportions of hydrogen, carbon dioxide, carbon monoxide and methane which are contained in the resulting syngas stream as a function of contact time in the reformer, temperature at exit, the amount of steam introduced, and to a lesser extent, pressure (FIG. 2). Certain proportions of syngas components are better than others for producing alcohols, while other proportions are preferred for producing alkanes. Generally speaking, if one wants to produce alkanes, one prefers a syngas stream containing more carbon monoxide and methane relative to hydrogen than is desired when one wishes to produce ethanol or methanol.

FIG. 2 graphs the approximate syngas content as a function of contact time for a feedstock converter run on wood, with an exit gas temperature of 898° C. (1650° F.) to 926° C. (1700° F.) Water content and the mole percents of other constituents in the gas are not shown in FIG. 2. Ninety-nine percent conversion occurs at 0.4 seconds. As can be seen, as contact time increases, the amount of hydrogen obtained increases, the amount of carbon monoxide decreases, the amount of carbon dioxide increases, and the amount of methane decreases slightly. By adjusting the contact time, one can optimize these ingredients for the production of alcohols. Generally speaking, one wants a contact time of from about 0.4 seconds to about 5.0 seconds, with from about 1.0 seconds to about 3.0 seconds being preferred for the production of ethanol. It is most preferable to operate at an exit temperature of about 898° C. (1650° F.) to about 926° C. (1700° F.) with about 1.0 seconds to about 2.0 seconds contact time in the reformer. Contact time is calculated by dividing the internal volume of the reformer by the flow rate of the syngas exiting the reformer. FIG. 2 would, of course, look different for different operating feedstock, as well as different amounts of steam and different temperatures and pressures.

The amount of superheated steam 1 used is a function of the nature of the feedstock used. Steam provides the additional hydrogen necessary to maximize alcohol production from the feedstock. In terms of the carbon to hydrogen stoichiometric ratio in lower alcohols such as methanol and ethanol, dry feedstock typically has a stoichiometric excess of carbon relative to hydrogen. Thus water, either trapped in the feedstock or in the form of superheated steam, or both, provides additional hydrogen to maximize alcohol production. Preferably, the feedstock is relatively dry, and the water necessary is provided in the form of added superheated steam. For making alcohol from wood feedstock, one preferably uses from about 0.14 kilograms (0.3 pounds) to about 0.18 kilograms (0.4 pounds) of steam per pound of "dry" feedstock. Since the "dry" feedstock in our process contains about 9% to about 15% moisture, one has a total water to wood ratio of about 0.4 to 0.5. This results in a fairly efficient operation.

Exemplary feedstock which can be used include: lignite, coal, red cedar, southern pine, hardwoods such as oak, cedar, maple and ash, bagasse, rice hulls, rice straw, kennaf (a weed), sewer sludge, motor oil, oil shale, creosote, pyrolysis oil from a tire pyrolysis plant, old railroad ties, dried distiller grains, corn stalks and cobs, animal excrement, and straw. The hydrogen and oxygen content for various different wood materials are shown in Table 1 below:

TABLE 1

| Type | Red Oak Sawdust | | Fir Mill Waste | | Furniture Waste | | Hybrid Poplar | | Alder/Fir Sawdust | |
|---|---|---|---|---|---|---|---|---|---|---|
| | As Rec'd | Dry | As Rec'd | Dry | As Rec'd | Dry | As Rec'd | Dry | As Rec'd | Dry |
| Carbon | 44.24 | 49.96 | 18.95 | 51.23 | 43.85 | 49.87 | 46.72 | 50.18 | 24.17 | 51.02 |
| Hydrogen | 5.24 | 5.92 | 2.21 | 5.98 | 5.2 | 5.91 | 5.64 | 6.06 | 2.75 | 5.8 |
| Oxygen (Note 1) | 38.76 | 43.77 | 15.66 | 42.29 | 35.42 | 40.29 | 37.66 | 40.44 | 18.25 | 38.54 |
| Nitrogen | 0.03 | 0.03 | 0.02 | 0.06 | 0.25 | 0.29 | 0.56 | 0.6 | 0.22 | 0.46 |
| Sulfur | <0.01 | 0.01 | 0.01 | 0.03 | 0.03 | 0.03 | 0.02 | 0.02 | 0.02 | 0.05 |
| Ash | 0.28 | 0.31 | 0.15 | 0.41 | 3.18 | 3.61 | 2.51 | 2.7 | 1.96 | 4.13 |
| Moisture | 11.45 | — | 63.00 | — | 12.07 | — | 6.89 | — | 52.63 | — |
| TOTAL | 100.00 | 100.00 | 100.00 | 100.00 | 100.00 | 100.00 | 100.00 | 100.00 | 100.00 | 100.00 |

Note 1:
Oxygen is not analyzed for in the sample.

Similar information is provided for several other feedstock in Table 2, except that the hydrogen and oxygen content is expressed on a "per carbon" basis:

TABLE 2

Chemical composition of raw materials

| Raw materials | wt % maf[a] | H/C | O/C (wt % mf[b]) | Ash |
|---|---|---|---|---|
| Birch wood | 48.4 | 0.12 | 0.95 | 0.2 |
| Bagasse | 47.3 | 0.13 | 0.98 | 1.6 |
| Olive wastes | 49.5 | 0.13 | 0.88 | 2.1 |
| *Miscanthus* pellets | 48.9 | 0.09 | 0.96 | 2.4 |
| Straw pellets | 47.0 | 0.13 | 0.99 | 6.2 |

[a]maf: moisture and ash-free material.
[b]mf: moisture-free material.

Reaction (1) is an illustrative assumption of the feedstock conversion reaction:

$$C_4H_6O_2 + C_4H_6O_3 + H_2O \rightarrow H_2 + CO + CO_2 + CH_4 \qquad (1)$$

The foregoing is, of course, merely illustrative, and is not expressed quantitatively. Those skilled in the art will appreciate that the actual hydrocarbon analysis for wood may vary significantly from this approximation. The quantitative content of the syngas stream will be determined as a function of feedstock used, quantity of steam used, reformation temperature and contact time in the reformer, as discussed above in connection with FIG. 2.

Syngas stream 3 passes from feedstock reformer 100 through a heat exchanger 110, where water 1a is preheated. The preheated water/steam then passes through heat exchanger 104, where it is further heated by flue gas from reformer 100 and becomes a stream of superheated steam 1 at a temperature of from about 454° C. (850°0 F.) to about 510° C. (950° F.) It is this superheated steam which is combined with feedstock stream 2 and is fed into feedstock reformer 100.

From heat exchanger 110, syngas stream 3 passes through a gas filtering device 120 and a cyclone 130, both of which are used to remove ash from syngas stream 3. Syngas stream 3 is then further washed and cooled with water in water washing unit 140. Water washing unit 140 comprises a column which is packed with conventional packing materials such as copper tubing, pall rings, metal mesh or other inert materials. Syngas stream 3 passes upwardly through the water washing column while water flows down through the upcoming syngas stream. The water wash serves to further cool syngas stream 3 to ambient temperature, and to remove any ash which may escape filter 120 and cyclone 130, though there should be no ash present unless there has been a rip in the filter bags of filter 120. Water from water washing unit 140 is recycled as stream 4. Stream 4 is de-gassed, filtered and passed through a carbon bed to remove organics. The water is then ready for re-use as needed in the system.

The syngas stream 3 at near ambient temperature passes through an oil-washing column 150. Column 150 is packed with conventional packing materials such as copper tubing, pall rings, metal mesh or other inert materials. Syngas stream 3 passes upwardly through oil washing column 150 while C-20 petroleum oil flows down through the upcoming syngas stream to remove any benzene, toluene, xylene or heavier hydrocarbons which may have been produced in feedstock reformer 100. The oil, benzene, toluene, xylene and heavier hydrocarbons exiting oil-washing column 150 are recycled as stream 16 through feedstock reformer 100.

Stream 3 then passes through an amine-scrubbing unit 160, which removes carbon dioxide from syngas stream 3. A pressure swing adsorbent (PSA) unit, discussed below in connection with hydrogen removal, could be used instead of an amine scrubber to remove the carbon dioxide. In this process the syngas is scrubbed with an amine based solvent in an absorption column. The solvent is regenerated in a second column thereby releasing a high purity $CO_2$ product. The carbon dioxide passes as stream 8 to Unit IV. Syngas stream 5, with the carbon dioxide removed, then passes on to Unit II.

Unit II: Syngas Compression and Hydrogen Removal

In Unit II, syngas stream 5 from Unit I, and syngas stream 13 from Unit V, are compressed in compressor 200, to a pressure of between 8273 KPa (1200 psi) and 16,547 KPa (2400 psi). The resulting compressed, mixed syngas stream (a mixture of streams 5 and 13) is fed to a pressure swing adsorbent (PSA) unit 210, which is used to remove a portion of the hydrogen (stream 10) from syngas stream 5 and 13. Pressure swing adsorption (PSA) is an adiabatic process and is applied for partial hydrogen removal from syngas by removing some of the hydrogen by adsorption through suitable adsorbents in fixed beds contained in pressure vessels under high pressure. Regeneration of adsorbents is accomplished by countercurrent depressurization and by purging at low pressure with previously recovered hydrogen gas. To obtain a continuous flow of product, a minimum of two adsorbers is needed, such that at least one adsorber is receiving feed gas. Simultaneously, the subsequent steps of depressurization, purging and repressurization back to the adsorption pressure are executed by the other adsorber(s). After such adsorbent regeneration and repressurization the adsorber is switched onto adsorption duty, whereupon another adsorber is regenerated. For removing hydrogen, the adsorbent used is silica gel.

An alternative type of hydrogen separator which might be used to separate a portion of the hydrogen from the syngas stream would be a hydrogen specific permeable membrane separator.

The amount of hydrogen removed from syngas stream 5 and 13 is controlled by controlling the ratio of syngas which is fed into PSA Unit 210, to that which is diverted by valve 211 to bypass PSA Unit 210. Gas chromatographic analysis is used to determine whether the hydrogen content of syngas stream 6 feeding to ethanol reactor 300 is that which is desired. Sufficient hydrogen is removed in PSA Unit 210 to leave a syngas stream 6 in which the molar ratio of hydrogen to carbon monoxide is about 1.1:1 to about 1.3:1, preferably 1.1:1.0. Recycle stream 17 may also be monitored. If excess internally produced hydrogen builds up in recycle stream 17, one might have the system divert even more hydrogen to stream 10 being diverted to reactor 400.

Unreacted hydrogen in ethanol reactor 300 is recycled (stream 17) and combined with syngas stream 6 as it enters ethanol reactor 300, thus increasing the molar ratio of hydrogen to carbon monoxide in reactor 300. Ideally, 2 moles of hydrogen react with 1 mole of carbon monoxide and 1 mole of methanol to produce 1 mole of ethanol and 1 mole of water.

The removed hydrogen stream 10 is conveyed to Fischer-Tropsch reactor 400 in Unit IV, which is catalyzed to produce methanol. The remaining syngas stream 6 passes over scavenger beds 220, commonly referred to in the art as "guard cat beds," which remove any chlorine, sulfur or heavy hydrocarbon impurities from syngas stream 6. Exemplary materials which may be used in beds 220 include activated carbon to remove hydrocarbons, zinc oxide to remove sulfur and silica gel to remove chlorides.

Unit III: Ethanol Production

After leaving guard cat beds 220, syngas stream 6 passes to said ethanol catalyzed Fischer-Tropsch reactor 300, at a pressure of between about 4481 KPa (650 psi) and about 13,790 KPa (2000 psi). It is joined by recycling syngas stream 17, and methanol stream 11 from methanol reactor 400. The combined stream is fed to ethanol catalyzed Fischer-Tropsch reactor 300. Syngas stream 17 is fed under pressure via compressor so that its pressure at least equals the pressure in the line feeding stream 6. Similarly, liquid methanol stream 11 is pumped into the line carrying syngas streams 6 and 17. All three lines are equipped with check valves to make certain that there is no back flow into the respective lines.

Fischer-Tropsch reactor 300 comprises a series of stainless steel tubes, each approximately 25 millimeters (1 inch) to 51 millimeters (2 inches) in inside diameter. The tubes are loaded with a catalyst which favors the production of ethanol. Larger diameter tubes give more production capacity, but also allow for the generation of more heat, which it is deleterious to the catalyst. Thus, the tube diameter is usually selected as a compromise between flow through capacity desired and the ease with which the heat can be controlled.

The production of ethanol generates considerably more heat than does the production of methanol. One has to remove about 2.6 times as much heat from an ethanol catalyzed Fischer-Tropsch reactor as from a Fischer-Tropsch reactor catalyzed to produce methanol.

The threshold temperature for ethanol production is about 260° C. at the pressures at which this reactor operates. This elevated temperature is imparted to the syngas stream in part through compression in syngas compressor 200, and in part through heat exchange with the reaction products of ethanol reactor 300 using conventional heat exchange techniques and equipment. The ethanol reactor operates at from about 300° C. to about 500° C., and a pressure of from about 4481 KPa (650 psi) to about 13,790 KPa (2000 psi). The gas hourly space velocity of the ethanol reactor is between 8,000 per hour and 50,000 per hour.

In reactor 300, a great deal of heat is generated which must be removed from the interior of the reactor to keep it from overheating. In the preferred embodiment, heat is removed and temperature controlled within reactor 300 by introducing a C-20 petroleum oil directly into the reactor tubes. Jacket cooling is also employed in addition, or as an alternative, but direct oil cooling is preferred. The oil passing through the reaction tubes of reactor 300 is cooled by removing it from the reactor and passing it through a heat exchanger where it boils water to create steam for use as needed in the system. The gaseous reactants and reaction products are passing through the oil as it is pumped through the reactor.

A unique ethanol catalyst is employed in the preferred embodiment. Although it probably catalyzes the formation of some methanol, the catalyst is designed to favor the production of ethanol from methanol feedstock, rather thin to produce methanol in the same reactor which then converts it to ethanol. Reactor 300 relies on methanol coming from methanol reactor 400 for conversion to ethanol.

The catalyst consists essentially of elemental cobalt as its primary constituent, with minor amounts of manganese, zinc, chromium and/or aluminum, and an alkali or alkaline earth promoter, with potassium carbonate being preferred for economic reasons. Preferably, it comprises on a metal elemental basis ex binder from about 65% to about 75% elemental cobalt, about 4% to about 12% manganese, about 4% to about 10% zinc, about 6% to about 10% chromium and/or about 6% to about 10% aluminum.

While the catalyst as used consists primarily of the above elements in their elemental form, the catalyst begins as a mixture of metal salts. Nitrates or carbonates are typically used. The catalyst goes through a "conditioning" process. In the conditioning process, the salts are largely reduced to their metallic elements, with some oxides remaining to form a lattice structure referred to as "spinels." The spinels help give the catalyst its overall spatial structure.

The catalyst may be used in its "pure" (or concentrated) form, or it may be diluted with carbon, by loading onto carbon pellets. The latter is often referred to as a supported catalyst. A pure catalyst will tend to run hotter than a supported catalyst, creating a process cooling challenge. On the other hand, a more pure catalyst will be more active and hence can be used at lower reaction temperatures. If lower reaction temperatures can be used, the catalyst will last longer. Thus, a compromise must often be reached between the desirability of using a more active catalyst and the need to dilute it somewhat in order to facilitate temperature control.

To prepare the catalyst for use in its pure form, the salts in appropriate proportions are combined with about 3% to about 4% by weight of a binder and about ¼% to about ¾% lubricant. The salts, binder and lubricant mixture are pelletized in a pelletizer—basically a tableting machine—where pellets 4 millimeters to 6 millimeters in diameter and 6 millimeters to 10 millimeters in length are pressed at approximately 262,000 KPa (38,000 psi). The pellets are then calcined by heating them at a rate of about 60° C. per 10 minutes, to a temperature of around 450° C., where they are held for about two hours under a nitrogen blanket. The pellets are then allowed to cool, prior to conditioning.

A supported catalyst is prepared by slurrying carbon pellets in a solution of the catalyst salts in appropriate proportions. The surface area of the carbon pellets is typically around 1200 square meters per gram. The water is evaporated off to leave catalyst loaded pellets. This process may have to be repeated to obtain the desired ratio of catalyst to carbon pellet. The catalyst loaded carbon pellets typically comprise from about 20% to about 40% catalyst. The catalyst loaded pellets need to be small enough to be packed into the reaction tubes. One wants to avoid dust, because it packs and clogs the tubes. Preferably, the pellets are from about 2 millimeters to about 4 millimeters in diameter, and from about 4 millimeters to about 10 millimeters long.

Either the pure catalyst pellets or the catalyst loaded carbon pellets must then be conditioned before being used. The conditioning process involves passing reducer-doped nitrogen over beds of the pellets. Initially, one begins with nitrogen doped with about 1% hydrogen. The doped gas is preheated to about 200° C., and as it passes over the catalyst bed, a reduction process is initiated which is exothermic and causes the reaction bed to heat to about 400° C. The reaction is initially carried on at a pressure of about 172 KPa (25 psig) to about 207 KPa (30 psig).

As the process proceeds, one measures the bed temperature and the gas temperature. As the temperature falls off, one adds additional amounts of hydrogen, building up to a level of about 25% to about 30% hydrogen. Pressure is also gradually increased over time, until it reaches about 4137 KPa (600 psig) to about 6895 KPa (1000 psig). After additional hydrogen ceases to be effective in maintaining temperature, carbon monoxide is added to the reaction stream. Syngas can be used as a source of carbon monoxide. Some of the hydrogen is replaced with the syngas or carbon monoxide stream.

The conditioned catalyst pellets are then cooled and put into drums under an inert gas purge, e.g., a nitrogen blanket. One cannot allow air to get to the catalyst. It is important that the catalyst be substantially free of oxygen. To the extent oxygen is contained in the catalyst, it reacts with hydrogen in the ethanol reactor and releases a great deal of excess and unwanted heat. Temperatures can rise to as high as about 1600° C.

It has been found that the present method produces about 0.11 kilograms (0.25 pounds) to about 0.14 kilograms (0.30 pounds) of ethanol per hour per pound of catalyst.

A number of reactions occur in ethanol catalyzed reactor 300, with the primary reactions being as follows:

$$2CO + H_2 + CH_3OH \rightarrow C_2H_5OH + CO_2 \quad (2)$$

$$CO + 2H_2 + CH_3OH \rightarrow C_2H_5OH + H_2O \quad (3)$$

$$2CH_3OH \rightarrow C_2H_5OH + H_2O \quad (4)$$

$$CO + 2H_2 \leftrightarrow CH_3OH \quad (5)$$

$$CO + H_2O \leftrightarrow CO_2 + H_2 \quad (6)$$

$$2CO + 2H_2 \leftrightarrow CH_4 + CO_2 \quad (7)$$

$$CO + 3H_2 \leftrightarrow CH_4 + H_2O \quad (8)$$

The reactions of primary importance are reactions (2-5). Reactions (2)-(4) are important because they form ethanol. Reaction (5) forms methanol, some of which reacts in reactions (2), (3) and (4), and some of which is recycled from the alcohol distillation. Reactions (7) and (8) take place to some extent, requiring ultimately some conversion of methane to carbon monoxide and hydrogen in the methane reformer (also referred to as the recycle reformer), though some methane may be recycled to the feedstock reformer to minimize the ongoing generation of methane in the feedstock reformer.

Notwithstanding the fact that the catalyst is designed to form ethanol, it is probable that some methanol is also being formed in the ethanol reactor. It is desirable to have methanol present in stoichiometric excess, as it tends to drive the reaction towards production of ethanol. Some higher alcohols and some alkanes are also formed. A small amount of carbon dioxide and methane are formed in ethanol reactor 300. Small amounts of methyl and ethyl formate are also formed in an equilibrium reaction.

The reaction products from ethanol reactor 300 pass to cooling and separation unit 310. Here, the alcohols are cooled to liquids and are separated from the gaseous elements, hydrogen, carbon monoxide and methane. The alcohols pass as stream 7 to an alcohol distillation unit. The gases are carried on to another amine scrubbing unit 320, or a PSA unit, which separates the carbon dioxide into stream 9 from the remaining gases, hydrogen, carbon monoxide, methane and other minor amounts of gases which pass to recycle stream 17, and a portion of which are bled off as purge gas stream 12 at valve 321. The recycling methyl and ethyl formate keep more from forming during the reaction.

Alcohol cooling and separation unit 310 comprises two coolers. One is a cross exchange unit and one is a water cooling tower. The cooled liquid/gas stream passes to a gas/liquid separator, with the liquid being passed by a stream 7 to the distillation column and the gas stream passing to a carbon dioxide separator 320. The separated carbon dioxide stream 9 is recycled to the methanol catalyzed Fischer-Tropsch reactor 400.

Unit IV: The Methanol Reactor (MR)

Hydrogen stream 10 from Unit II, carbon dioxide stream 8 from Unit I and carbon dioxide stream 9 from Unit III are fed through a surge tank 401 to Fischer-Tropsch reactor 400 which is catalyzed to favor the production of methanol (the methanol reactor). Its construction is the same as that of ethanol reactor 300. The catalyst used is a conventional methanol catalyst, primarily copper, with a minor amount of an alkali metal promoter. As received, they comprise copper oxide, zinc oxide, aluminum oxide and an alkali metal promoter. Copper oxide comprises about 50% to about 60%, preferably 55%, zinc oxide from about 21% to about 25%, aluminum oxide from about 8% to about 10% and the other ingredients being precedent in minor amounts. As with the ethanol catalyst, the methanol catalyst must be conditioned prior to use, such that it substantially comprises the metals in elemental form.

Methanol reactor 400 is operated under a pressure of 4137 KPa (650 psig) to about 13,790 KPa (2000 psig) and at a temperature of 260° C. to 305° C. The gas hourly space velocity in the methanol reactor is from about 15,000 per hour to about 110,000 per hour. The pressure in hydrogen stream 10 is adjusted as necessary to 4137 KPa (650 psi) to 13,790 KPa (2000 psi). A compressor is used to pressurize carbon dioxide stream 8 coming from Unit I. Similarly, a compressor is used to compress carbon dioxide stream 9 coming from Unit III. All three lines are thus introduced into reactor 400 at the operating pressure of reactor 400, and each line includes a back flow check valve.

As they are fed from surge tank 401, carbon dioxide streams 8 and 9 are combined with hydrogen stream 10. The combined reactant streams 8-10 are preheated to the threshold reaction temperature of 260° C. to 305° C. by heat exchange with the product stream exiting the reactor, and/or as part of a heat exchange system for the reactor itself. As with the ethanol reactor, heat in methanol reactor 400 has to be controlled by removing some of the exothermic heat of reaction. This may be accomplished in methanol reactor 400 by oil cooling, as is done in the ethanol reactor 300, or by withdrawing gases from the reactor, cooling them in a heat exchanger, and returning them to the reactor.

Surge tank 401 offers the operator a way of controlling peaks and valleys which may occur from time to time in the carbon dioxide content of the reaction system. Appropriate controls can be employed for accomplishing this automatically.

The principle methanol reaction between carbon dioxide and hydrogen is as follows:

$$3H_2 + CO_2 \leftrightarrow CH_3OH + H_2O \quad (9)$$

To some extent, other reactions also occur, but the methanol reaction (9) is predominant.

The reaction products from methanol reactor 400 are passed to a cooling and separation station 410. Cooling is accomplished by heat exchange with incoming reactants, with water, and/or in a water cooling tower. The cooled liquid and gas products are separated in a liquid gas separator and the liquids are passed to a distillation column 420. Unreacted gaseous hydrogen and carbon dioxide as well as any methane which may have been formed are simply recycled back into reactor 400. Distilled methanol stream 11 is passed to Unit III where it is introduced into the ethanol reactor 300. Water stream 14 is recycled to Unit I where it is joined with incoming water stream 1a and converted to superheated steam 1.

Unit V: The Methane Reformer

When the methane content in recycling syngas stream 17 reaches about 30%, valve 321 is operated to divert the syngas stream or a portion thereof, as stream 12, to methane reformer 500, via a methane surge tank 501. Surge tank 501 serves the same purpose for methane as is served by surge tank 401 for carbon dioxide. It may also be automatically controlled.

Methane reformer 500 is constructed in a standard manner. In reformer 500, the methane component of syngas stream 12 is reacted with steam, fed as stream 15 into reformer 500. A conventional nickel catalyst is used. The steam used may be independently heated, or may be diverted from stream 1, generated at heat recovery unit 110 and heat exchanger 104. The reaction is carried on at 843° C. (1550° F.) to 898° C. (1650° F.), 1034 KPa (150 psig) to 2758 KPa (400 psig), and a gas hourly space velocity (GHSV) of 11,000 per hour.

The reaction of the steam and the methane in gas stream 12 is basically as follows:

$$CH_4 + H_2O \leftrightarrow CO + 3H_2 \quad (10)$$

The reaction products proceed to a cooling and separation unit 510 where syngas stream 13 is separated from unreacted water (stream 19). Syngas stream 13 contains the carbon monoxide and hydrogen generated in methane reformer 500, as well as any hydrogen and carbon monoxide which was contained in entry syngas stream 12. Recovered water is recycled and converted to steam for introduction ultimately into steam stream 15 or stream 1.

Illustrative Reaction Scheme

The following is an illustrative reaction scheme. It is theoretical in nature, and does not take into consideration every reaction that is occurring in the process of the present invention. For example, the illustration ignores completely reaction (7) of carbon monoxide and hydrogen to methane and carbon dioxide, and the various reactions which form methanol in the ethanol reactor. Also, the reactions are not shown quantitatively. Accordingly, this illustration is merely for purposes of helping to illustrate how the process flows, and is not intended and should not be interpreted as being a quantitative representation. The various reactions used in the following scheme have(been discussed above, and accordingly are labeled with the same numbers they have been given above.

To help one follow the flow, the reaction scheme indicates where the various reaction products will flow. Thus of hydrogen produced in the feedstock reaction, some will be diverted to the methanol reactor at hydrogen removal unit 210. The rest will flow with the carbon monoxide and methane into the ethanol reactor. This is in keeping with the discussion above, which suggests allowing about 1 to about 1.1 parts of hydrogen per one part of carbon monoxide to continue in the syngas stream to the ethanol reactor, while diverting the rest to the methanol reactor.

For each successive reaction, any ingredients or portions of ingredients which do not participate in the reaction are indicated as being recycled or as passing through the reactor. The reaction scheme includes two passes through the methanol and ethanol reactors. Obviously in actual practice, the process is ongoing such that the reactions will not flow linearly to completion of a single overall reaction.

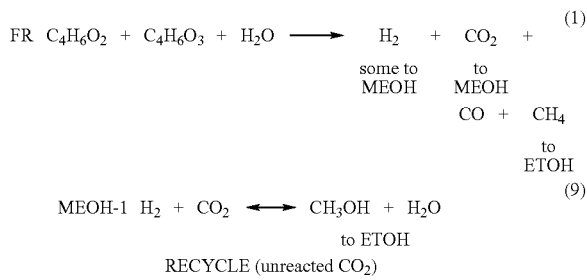

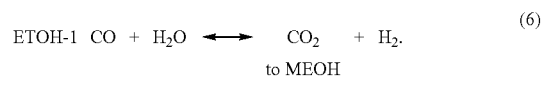

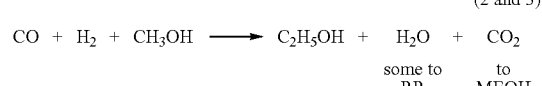

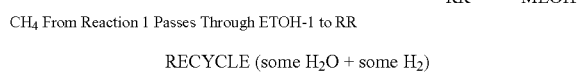

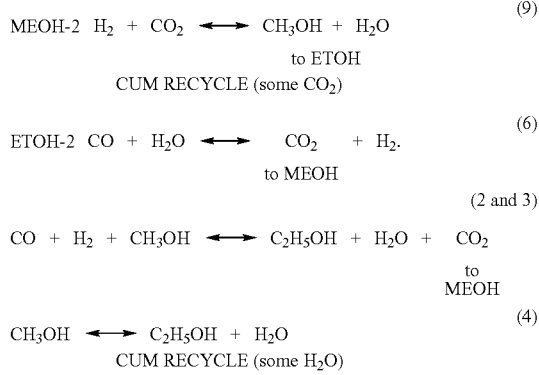

The legends underneath feedstock reformation reaction (1) show the diversion of the carbon dioxide and some of the hydrogen to the methanol reactor, with the rest of the syngas stream including hydrogen, carbon monoxide and methane, going to the ethanol reactor. The reactions occurring in the methanol and ethanol reactors are numbered, illustrating different passes of the reactants through the reactors as they cycle through the process.

The MEOH-1 reaction shows the reaction products going on to the ethanol reactor, with unused carbon dioxide being recycled. The ETOH-1 reactions illustrate several different reactions which can be occurring in the ethanol reactor at the same time. The ETOH-1 reactions illustrate how reaction (6) can produce enough hydrogen internally to supplement the conversion of carbon monoxide and methanol to ethanol in reaction (2). Reactions (2) and (3) have been combined in this illustrative reaction scheme. As illustrated, reaction (6) in ETOH-1 produces an excess of hydrogen which is then recycled in the ethanol reactor. Carbon dioxide produced in reaction (6) is removed as shown in FIG. 1 and forwarded to the methanol reactor as carbon dioxide stream 9. Carbon dioxide formed in reaction 3 is removed via scrubber 320, and the hydrogen would be part of recycle stream 17 going back through ethanol reactor 300.

ETOH-1 reaction (2) illustrates the formation of ethanol from carbon monoxide and hydrogen from the syngas stream, as well as hydrogen produced in ethanol reactor 300 by reaction 4, and from methanol introduced in methanol reactor 400. A portion of the water formed is shown as being diverted to the methane recycle reformer along with the methane which is indicated as being a "pass through" in the ethanol reactor. As noted above, the methane and water produced would actually recycle until such time as it is determined that some of the methane should be bled off and either diverted to the recycle reformer 500 or back to feedstock reactor 100, as discussed above. Showing a portion of the water and the methane as proceeding directly to the recycle reformer is thus only for illustrative purposes. The unreacted water shown as coming into ETOH-1 from MEOH-1, along with water produced in ETOH-1, to the extent not diverted to the recycle reformer, are shown as part of the recycle stream for the ethanol reactor.

The recycle reformer reaction RR (10) illustrates the conversion of methane to carbon monoxide and hydrogen by reaction with steam. The carbon monoxide and hydrogen are sent via stream 13 to syngas compression unit 200, and a portion of the hydrogen is shown as being diverted to the methanol reactor via hydrogen removal unit 210, as hydrogen stream 10.

MEOH-2 then shows the reaction of hydrogen which has been diverted to the methanol reactor with more of the carbon dioxide to yield additional methanol and water. These are shown as being conveyed to the ethanol reactor, via stream 11. The cumulative recycle of carbon dioxide in unit IV is also indicated.

ETOH-2 shows a repeat of reactions (2)-(4) as well as reaction (6), based on the reactant inputs received from the various reactions discussed above. The hydrogen formed in reaction (6) in the ETOH-2 pass is used internally in reaction (2). The ETOH-2 reaction (3) forms carbon dioxide which would normally be sent to the methanol reactor.

As discussed above, this reaction is illustrative only, to demonstrate how the various reactants will flow through the process. It is not shown quantitatively. In actual practice, the hydrocarbon content of the feedstock used will vary, yields will vary, and other reactions will take place in the process. The foregoing is an illustrative discussion only.

Conclusion

The preferred embodiments discussed above provide for efficient handling and processing of feedstock to useful end products, the preferred end product in this case being ethanol. By varying contact time and conditions in the feedstock reformer, one can optimize the syngas stream for the production of the desired end product.

The syngas stream products are utilized efficiently to optimize yields. The internal production of hydrogen, the use of carbon dioxide and hydrogen to first form methanol in one reactor and then combine the resulting methanol with the remaining syngas stream in a reactor especially catalyzed to favor the production of ethanol, further help optimize ethanol production.

The recycling of methane to the feedstock reformer helps minimize the generation of further methane. Alternatively, recycling the methane through a reformer with steam creates carbon monoxide and hydrogen which can be reinjected into the syngas stream to provide further raw materials for forming ethanol.

Of course, it is understood that the foregoing are merely preferred embodiments of the invention and that various changes and alterations can be made without departing from the spirit and broader aspects of the invention.

The invention claimed is:

1. A process for converting carbonaceous feedstock to alcohol comprising:
   reforming carbonaceous feedstock into a first syngas stream comprising hydrogen, carbon dioxide and carbon monoxide;
   separating the carbon dioxide and a portion of the hydrogen from said first syngas stream, to yield a second syngas stream comprising a reduced amount of hydrogen and carbon monoxide;
   passing said separated hydrogen and carbon dioxide through a first catalyzed reactor to produce methanol;
   passing said methanol from said first catalyzed reactor, and said second syngas stream, through a second catalyzed reactor to produce ethanol.

2. The process of claim 1 in which methane formed in the process is passed with steam through a methane reformer to produce carbon monoxide and hydrogen; said carbon monoxide and hydrogen formed in said methane reformer being also passed through said second catalyzed reactor.

3. The process of claim 2 in which carbon dioxide leaving said second catalyzed reactor is also passed through said first catalyzed reactor.

4. The process of claim 3 in which the amount of hydrogen removed from said syngas stream is adjusted such that the ratio of hydrogen to carbon monoxide passing through said second catalyzed reactor is from about 1.1:1.0 to about 1.3:1.0.

5. The process of claim 3 in which the amount of hydrogen removed from said syngas stream is adjusted such that the ratio of hydrogen to carbon monoxide passing through said second catalyzed reactor is about 1.1:1.0.

6. The process of claim 4 in which unreacted carbon dioxide and hydrogen issuing from said first catalyzed reactor are recycled back through said reactor.

7. The process of claim 6 in which unreacted carbon monoxide and hydrogen issuing from said second catalyzed reactor are recycled back through said second catalyzed reactor.

8. The process of claim 6 in which methane produced in said process is allowed to recycle back through said second catalyzed reactor with unreacted hydrogen and carbon monoxide; except that at least some of the time, at least a portion of said unreacted hydrogen, unreacted carbon monoxide and methane stream is diverted to said methane reformer.

9. The process of claim 8 in which methanol exiting said second catalyzed reactor is recycled back through said second catalyzed reactor.

10. The process of claim 4 in which carbon dioxide is separated from said first syngas stream before hydrogen is separated from it, and a portion of the resulting syngas stream is diverted and is used to run a turbine to generate electricity to power compressors and other electrically driven devices used in the process.

11. The process of claim 1 in which said second catalyzed reactor is catalyzed by a catalyst consisting essentially of elemental cobalt as its primary constituent, with minor amounts of manganese, zinc and one of chromium, aluminum and mixtures thereof.

12. The process of claim 11 in which said catalyst additionally includes an alkali or alkaline earth promoter.

13. The process of claim 12 in which said catalyst consists essentially of from about 65% to about 75% elemental cobalt, about 4% to about 12% manganese, about 4% to about 10% zinc, and about 6% to about 10% of one of chromium, aluminum or mixtures thereof.

14. The process of claim 11 in which said catalyst consists essentially of from about 65% to about 75% elemental cobalt, about 4% to about 12% manganese, about 4% to about 10% zinc, and about 6% to about 10% of one of chromium, aluminum or mixtures thereof.

15. The process of claim 13 in which methane formed in the process is passed with steam through a methane reformer to produce carbon monoxide and hydrogen; said carbon monoxide and hydrogen formed in said methane reformer being also passed through said second catalyzed reactor.

16. The process of claim 15 in which carbon dioxide leaving said second catalyzed reactor is also passed through said first catalyzed reactor.

17. The process of claim 16 in which the amount of hydrogen removed from said syngas stream is adjusted such that the ratio of hydrogen to carbon monoxide passing through said second catalyzed reactor is from about 1.1:1.0 to about 1.3:1.0.

18. The process of claim 11 in which methane formed in the process is passed with steam through a methane reformer to produce carbon monoxide and hydrogen; said carbon monoxide and hydrogen formed in said methane reformer being also passed through said second catalyzed reactor.

19. The process of claim 18 in which carbon dioxide leaving said second catalyzed reactor is also passed through said first catalyzed reactor.

20. The process of claim 19 in which the amount of hydrogen removed from said syngas stream is adjusted such that the ratio of hydrogen to carbon monoxide passing through said second catalyzed reactor is from about 1.1:1.0 to about 1.3:1.0.

21. A process for converting carbonaceous feedstock to alcohol comprising:
reforming carbonaceous feedstock into a first syngas stream comprising hydrogen, carbon dioxide and carbon monoxide;
separating the carbon dioxide and a portion of the hydrogen from said first syngas stream, to yield a second syngas stream comprising a reduced amount of hydrogen and carbon monoxide;
passing said separated hydrogen and carbon dioxide through a first catalyzed reactor to produce methanol;
passing said methanol from said first catalyzed reactor, and said second syngas stream, through a second catalyzed reactor to produce ethanol;
wherein said step of reforming said carbonaceous feedstock is conducted at elevated temperature in a feedstock reformer, and includes adjusting the contact time of the syngas at elevated temperatures in the reformer, and adjusting the exit gas temperature of the syngas as it leaves the reformer, to achieve proportions of carbon monoxide, hydrogen and methane most closely approximating those desired given the intended use of the syngas.

22. The process of claim 21 which includes
introducing said feedstock and superheated steam into the feedstock reformer at about 204° C. (400° F.);
adjusting said exit temperature of said syngas leaving said feedstock reformer to between about 871° C. (1600° F.) and about 1204° C. (2200° F.);
adjusting said contact time of said syngas within said reformer within a range of from about 0.4 seconds to about 5.0 seconds.

23. The process of claim 22 in which said syngas exit temperature and contact time are adjusted to produce a syngas most optimally proportioned to produce lower alcohols, by adjusting said syngas exit temperature to from about 898° C. (1650° F.) to about 926° C. (1700° F.), and said contact time from about 1.0 seconds to about 3.0 seconds.

24. The process of claim 23 in which said contact time is adjusted to from about 1.0 seconds to about 2.0 seconds.

25. The process of claim 22 in which methane formed in the process is passed with steam through a methane reformer to produce carbon monoxide and hydrogen; said carbon monoxide and hydrogen formed in said methane reformer being also passed through said second catalyzed reactor.

26. The process of claim 25 in which carbon dioxide leaving said second catalyzed reactor is also passed through said first catalyzed reactor.

27. The process of claim 26 in which the amount of hydrogen removed from said syngas stream is adjusted such that the ratio of hydrogen to carbon monoxide passing through said second catalyzed reactor is from about 1.1:1.0 to about 1.3:1.0.

28. The process of claim 21 in which methane formed in the process is passed with steam through a methane reformer to produce carbon monoxide and hydrogen; said carbon monoxide and hydrogen formed in said methane reformer being also passed through said second catalyzed reactor.

29. The process of claim 28 in which carbon dioxide leaving said second catalyzed reactor is also passed through said first catalyzed reactor.

30. The process of claim 29 in which the amount of hydrogen removed from said syngas stream is adjusted such that the ratio of hydrogen to carbon monoxide passing through said second catalyzed reactor is from about 1.1:1.0 to about 1.3:1.0.

31. A process for converting carbonaceous feedstock to alcohol comprising:
reforming carbonaceous feedstock into a first syngas stream comprising hydrogen, carbon dioxide and carbon monoxide;
separating the carbon dioxide and a portion of the hydrogen from said first syngas stream, to yield a second syngas stream comprising a reduced amount of hydrogen and carbon monoxide;
passing said separated hydrogen and carbon dioxide through a first catalyzed reactor to produce methanol;
passing said methanol from said first catalyzed reactor, and said second syngas stream, through a second catalyzed reactor to produce ethanol;
wherein said step of reforming feedstock into a first syngas stream includes:
comminuting the feedstock; entraining the comminuted feedstock in a stream of inert gas and conveying it to a feed hopper where it is maintained in an inert gas environment;
metering the flow rate of feedstock into said reformer by a rotary valve through which the feedstock is fed, said rotary valve comprising a plurality of separate compartments which rotate from a valve inlet at which comminuted feedstock is fed into a valve compartment, to a valve outlet at which comminuted feedstock flows from said rotary valve;
feeding said feedstock through a feed conduit leading from said rotary valve outlet to a stream of steam under pressure into which the feedstock is fed and entrained;
feeding inert gas into said feed conduit under pressure, to prevent the steam under pressure from creating a back pressure in said feed conduit which would prevent comminuted feedstock from feeding into said stream of steam under pressure;
feeding inert gas under pressure into said rotary valve such that it pressurizes a compartment after it has passed said rotary valve inlet and before it has reached said rotary valve outlet whereby the comminuted feedstock contained in said compartment is maintained under pressure;
providing a vent in said rotary valve at a point between said outlet and said inlet, in the direction in which said compartments are rotated, such that a compartment under pressure which has been emptied at said outlet and is returning to said inlet will be, vented of pressure introduced when said inert gas is fed into said compartment under pressure, before the emptied compartment reaches said rotary valve inlet;
feeding the steam entrained stream of comminuted feedstock to a feedstock reformer.

32. The process of claim 31 in which said comminuted feedstock is dried to a moisture content of from about 5% to about 20% before being fed into said feed hopper.

33. The process of claim 32 in which said feedstock is dried to a moisture content of from about 9% to about 15% before it is fed into said feed hopper.

34. The process of claim 31 in which said stream of inert gas comprises flue gas.

35. The process of claim 34 in which said flue gas is the exhaust gas from the carbonaceous feedstock reformer into which the comminuted feedstock and steam are fed.

36. The process of claim 31 in which methane formed in the process is passed with steam through a methane reformer to produce carbon monoxide and hydrogen; said carbon monoxide and hydrogen formed in said methane reformer being also passed through said second catalyzed reactor.

37. The process of claim 36 in which carbon dioxide leaving said second catalyzed reactor is also passed through said first catalyzed reactor.

38. The process of claim 37 in which the amount of hydrogen removed from said syngas stream is adjusted such that the ratio of hydrogen to carbon monoxide passing through said second catalyzed reactor is from about 1.1:1.0 to about 1.3:1.0.

39. A process for converting carbonaceous feedstock to alcohol comprising:
reforming carbonaceous feedstock into a first syngas stream comprising hydrogen, carbon dioxide and carbon monoxide;
separating the carbon dioxide and a portion of the hydrogen from said first syngas stream, to yield a second syngas stream comprising a reduced amount of hydrogen and carbon monoxide;
passing said separated hydrogen and carbon dioxide through a first catalyzed reactor to produce methanol;
passing said methanol from said first catalyzed reactor, and said second syngas stream, through a second catalyzed reactor to produce ethanol;
wherein said step of reforming said carbonaceous feedstock is conducted at elevated temperature in a feedstock reformer, and includes adjusting the contact time of the syngas at elevated temperatures in the reformer, and adjusting the exit gas temperature of the syngas as it leaves the reformer, to achieve proportions of carbon monoxide, hydrogen and methane most closely approximating those desired given the intended use of the syngas; and in which said second catalyzed reactor is catalyzed by a catalyst consisting essentially of elemental cobalt as its primary constituent, with minor amounts of manganese, zinc and one of chromium, aluminum and mixtures thereof.

40. The process of claim 39 which includes introducing said feedstock and superheated steam into the feedstock reformer at about 204° C. (400° F.); adjusting said exit temperature of said syngas leaving said feedstock reformer to between about 871° C. (1600° F.) and about 1204° C. (2200° F.); adjusting said contact time of said syngas within said reformer within a range of from about 0.4 seconds to about 5.0 seconds.

41. The process of claim 40 in which said second catalyzed reactor is catalyzed by a catalyst consisting essentially of elemental cobalt as its primary constituent, with minor amounts of manganese, zinc and one of chromium, aluminum and mixtures thereof.

42. The process of claim 41 in which said catalyst consists essentially of from about 65% to about 75% elemental cobalt, about 4% to about 12% manganese, about 4% to about 10% zinc, and about 6% to about 10% of one of chromium, aluminum or mixtures thereof.

43. The process of claim 42 in which methane formed in the process is passed with steam through a methane reformer to produce carbon monoxide and hydrogen; said carbon monoxide and hydrogen formed in said methane reformer being also passed through said second catalyzed reactor.

44. The process of claim 43 in which carbon dioxide leaving said second catalyzed reactor is also passed through said first catalyzed reactor.

45. The process of claim 44 in which the amount of hydrogen removed from said syngas stream is adjusted such that the ratio of hydrogen to carbon monoxide passing through said second catalyzed reactor is from about 1.1:1.0 to about 1.3:1.0.

46. The process of claim 39 in which said step of reforming feedstock into a first syngas stream includes:
   comminuting the feedstock; entraining the comminuted feedstock in a stream of inert gas and conveying it to a feed hopper where it is maintained in an inert gas environment;
   metering the flow rate of feedstock into said reformer by a rotary valve through which the feedstock is fed, said rotary valve comprising a plurality of separate compartments which rotate from a valve inlet at which comminuted feedstock is fed into a valve compartment, to a valve outlet at which comminuted feedstock flows from said rotary valve;
   feeding said feedstock through a feed conduit leading from said rotary valve outlet to a stream of steam under pressure into which the feedstock is fed and entrained;
   feeding inert gas into said feed conduit under pressure, to prevent the steam under pressure from creating a back pressure in said feed conduit which would prevent comminuted feedstock from feeding into said stream of steam under pressure;
   feeding inert gas under pressure into said rotary valve such that it pressurizes a compartment after it has passed said rotary valve inlet and before it has reached said rotary valve outlet whereby the comminuted feedstock contained in said compartment is maintained under pressure;
   providing a vent in said rotary valve at a point between said outlet and said inlet, in the direction in which said compartments are rotated, such that a compartment under pressure which has been emptied at said outlet and is returning to said inlet will be vented of pressure introduced when said inert gas is fed into said compartment under pressure, before the emptied compartment reaches said rotary valve inlet;
   feeding the steam entrained stream of comminuted feedstock to a feedstock reformer.

47. The process of claim 46 in which said comminuted feedstock is dried to a moisture content of from about 5% to about 20% before being fed into said feed hopper.

48. The process of claim 47 in which said feedstock is dried to a moisture content of from about 9% to about 15% before it is fed into said feed hopper.

49. The process of claim 48 in which said stream of inert gas comprises flue gas.

50. The process of claim 49 in which said flue gas is the exhaust gas from the carbonaceous feedstock reformer into which the comminuted feedstock and steam are fed.

51. The process of claim 46 which includes introducing said feedstock and superheated steam into the feedstock reformer at about 204° C. (400° F.); adjusting said exit temperature of said syngas leaving said feedstock reformer to between about 871° C. (1600° F.) and about 1204° C. (2200° F.); adjusting said contact time of said syngas within said reformer within a range of from about 0.4 seconds to about 5.0 seconds.

52. The process of claim 51 in which said second catalyzed reactor is catalyzed by a catalyst consisting essentially of elemental cobalt as its primary constituent, with minor amounts of manganese, zinc and one of chromium, aluminum and mixtures thereof.

53. The process of claim 52 in which said catalyst consists essentially of from about 65% to about 75% elemental cobalt, about 4% to about 12% manganese, about 4% to about 10% zinc, and about 6% to about 10% of one of chromium, aluminum or mixtures thereof.

54. The process of claim 53 in which methane formed in the process is passed with steam through a methane reformer to produce carbon monoxide and hydrogen; said carbon monoxide and hydrogen formed in said methane reformer being also passed through said second catalyzed reactor.

55. The process of claim 54 in which carbon dioxide leaving said second catalyzed reactor is also passed through said first catalyzed reactor.

56. The process of claim 55 in which the amount of hydrogen removed from said syngas stream is adjusted such that the ratio of hydrogen to carbon monoxide passing through said second catalyzed reactor is from about 1.1:1.0 to about 1.3:1.0.

* * * * *